US00PP11629P

United States Patent [19]

Ogilvie

[11] Patent Number: Plant 11,629

[45] Date of Patent: Nov. 7, 2000

[54] SHRUB ROSE PLANT NAMED 'AC WILLIAM BOOTH'

[75] Inventor: Ian S. Ogilvie, Pointe Claire, Canada

[73] Assignee: Her Majesty the Queen in right of Canada, as represented by the Minister of Agriculture, Ontario, Canada

[21] Appl. No.: 09/196,433

[22] Filed: Nov. 19, 1998

[51] Int. Cl.[7] ..... A01H 5/00

[52] U.S. Cl. ..... Plt./102

[58] Field of Search ..... Plt./107, 102, 108, Plt./141, 149, 150, 151

[56] References Cited

PUBLICATIONS

Ogilvie, et al., 1999, "Three new winter–hardy Explorer rose cultivars", Hortscience 34(2): 358–360. (Dialog (R) File 50: CAB Abstracts.

*Primary Examiner*—Howard J. Locker

*Attorney, Agent, or Firm*—Burns, Doane, Swecker & Mathis, L.L.P.

[57] ABSTRACT

A new and distinct variety of shrub rose plant is provided which forms attractive dark red single blossoms that tend to lighten somewhat to pink when fully mature. The new variety exhibits a large arching shrub growth habit with dark green foliage that exhibits glossiness on the upper surface, and good winter hardiness. The blossoms are round when viewed from above with somewhat flattened upper and lower parts when viewed from the side. Good resistance to powdery mildew and blackspot have been observed. The leaflets most commonly number seven per leaf. The new variety propagates well by the use of soft wood stem cuttings, and is well adapted for growing as ornamentation in the landscape.

2 Drawing Sheets

SUMMARY OF THE INVENTION

The new *Rosa hybrida* variety of shrub rose plant of the present invention was selected during 1987 following artificial pollination carried out in 1984 at the Central Experimental Farm, Ottawa, Ontario, Canada. The female parent (i.e., the seed parent) was an unnamed line designated 'L83' (non-patented in the United States) and the male parent (i.e., the pollen parent) was an unnamed line designated 'A72' (non-patented in the United States). Each parent had been previously studied in the hope that it would contribute the desired attractive characteristics to the product of the cross. The 'L83' parent is described at HortScience 23(2):415 to 416 (1988) in an article entitled "Rose Germplasm L83". The 'A72' parent was obtained in 1980 by a cross between the 'Arthur Bell' variety (non-patented in the United States) and the 'Applejack' variety (non-patented in the United States). Following observation of the offspring of this cross a single plant of the new variety was observed and selected.

The parentage of the new variety can be summarized as follows:

'L83'×'A72'.

It was found that the new variety of shrub rose plant of the present invention possesses the following combination of characteristics:

(a) exhibits an arching growth habit with attractive dark green foliage that bears glossiness on the upper surface, (b) forms attractive dark red single blossoms that tend to fade to medium red when fully mature, (c) propagates well by the use of softwood cuttings, (d) exhibits good winter hardiness, (e) exhibits good resistance to powdery mildew and blackspot, and (f) is particularly well suited for growing as ornamentation in the landscape.

The rose plants of the new variety can be grown well on their own roots out-of-doors without protection at L'Assomption, Quebec, Canada. The blossoms commonly appear continuously for approximately ten weeks beginning in late-June. Resistance to powdery mildew and blackspot has been observed to date.

When compared to the 'John Cabot' variety (non-patented in the United States), the new variety of the present invention exhibits single blossoms while those of the 'John Cabot' variety are double, forms generally smaller blossoms, and forms generally smaller leaves.

The new variety well meets the needs of the horticultural industry. It can be grown to advantage as attractive ornamentation in parks, gardens, public areas, and residential landscapes.

The characteristics of the new variety have been found to be homogenous and stable and have been shown to be strictly transmissible by asexual propagation by the rooting of softwood stem cuttings conducted at L'Assomption, Quebec, Canada, beginning in 1985.

The new variety has been named the 'AC William Booth'. Also, the new variety is a member of the EXPLORER Series of hardy rose plants.

BRIEF DESCRIPTION OF THE PHOTOGRAPHS

The accompanying photographs show, as nearly true as it is reasonably possible to make the same in color illustrations of this character, typical specimens of mature plants and plant parts of the new variety. The illustrated rose plants of the new variety were two to three years of age and were photographed during 1995 while growing on their own roots at L'Assomption, Quebec, Canada.

FIG. 1 — illustrates a typical specimen of a blossom of the new variety. The glossy dark green foliage also is shown.

FIG. 2 — illustrates a typical flowering plant of the new variety while growing in the landscape. The arching growth habit, dark green glossy foliage, and single dark red fading to medium red blossoms are apparent.

DETAILED DESCRIPTION

The chart used in the identification of colors is that of The Royal Horticultural Society (R.H.S. Colour Chart). Common color terms are to be accorded their ordinary dictionary significance. The description is based on the observation of mature plants of the new variety while being grown outdoors at L'Assomption, Quebec, Canada.

Class: Shrub.

Plant:

*Height.*—A mature plant commonly assumes a height of up to approximately 1 m. and a width of approximately 2 m. at the end of the growing season.

*Habit.*—Arching.

Thorns: Quantity: Medium. Quantity and size: Medium number of long thorns (greater than 5 mm. in length) and the sparse presence of short thorns. Color: Green Group 139C with tones of Greyed-Purple Group 185B. Configuration: Deep concave.

Leaves: Compound and pinnate.

Figure 1:
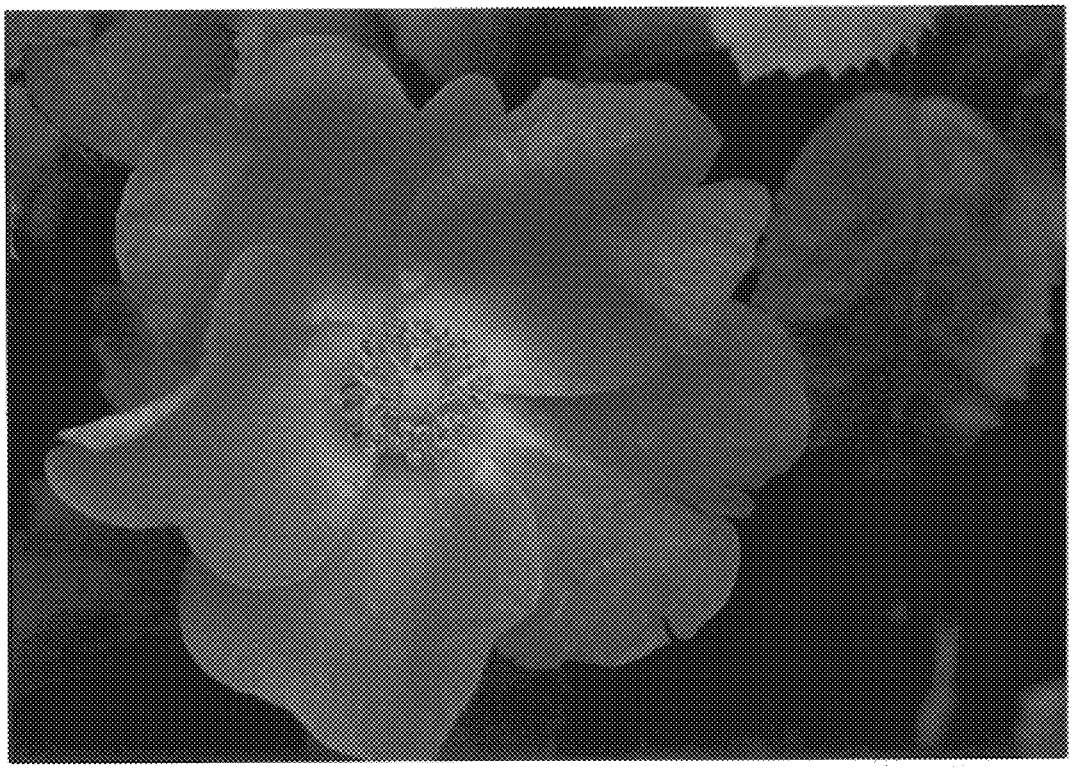
Figure 2:
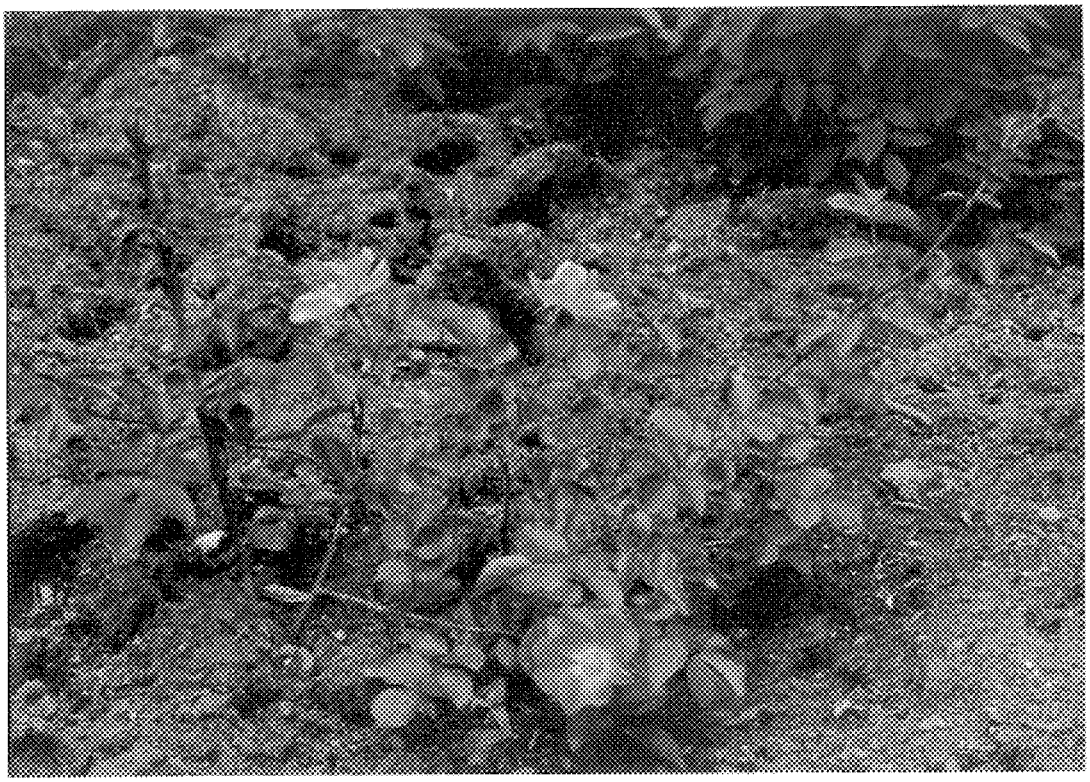

*Leaflets.*—Number: 3, 5, and 7 (most common). Shape: Elliptic (as illustrated in FIG. 2) with a rounded base. Margins: Serrate. Size: Commonly approximately 75 to 110 mm. (90 mm. mean) in length and approximately 55 to 100 mm. (72 mm. mean) in width on average. Texture: Leathery. General appearance: Dark green with strong glossiness on the upper surface.

*Color.*—Adult foliage: Dark green, Yellow-Green Group 147A on upper surface and Yellow-Green Group 148A to 147C on under surface depending on the age. Young foliage: Green Group 137B with Greyed-Purple Group 184A on the upper surface and Green Group 137D with Greyed-Purple Group 184B on the under surface. Young shoots: Bear very strong anthocyanin coloration.

*Petiole.*—Greyed-Purple Group 184A on upper surface and Green Group 138B on under surface.

*Stipule.*—Green Group 138B with tones of Greyed-Purple Group 183C.

Inflorescence:

*Number of flowers.*—Commonly approximately 4 to 14 per shoot in clusters.

*Peduncle.*—Commonly bears many thorns. Green Group 138A and 138B with Red-Purple Group 59B.

*Sepals.*—With medium extensions, and commonly approximately 12 to 15 mm. (14 mm. mean) in length. Green Group 138C and 138D on the upper surface and Green Group 138A and 138B with Red-Purple Group 59B on the under surface.

*Buds.*—Shape: Pointed in longitudinal section. Color upon opening: Red-Purple Group 57A on the upper surface and Red Group 61C on the under surface.

*Flower.*—Shape: Single, round when viewed from above with flat upper and lower parts. Diameter: Commonly approximately 40 to 60 mm. (50 mm. mean). Color (when blooming): The overall blossom coloration initially is Red-Purple Group 57A, and when open the upper petal surface is Red-Purple Group 57A and under petal surface is Red-Purple Group 57C. The coloration of the blossoms commonly fades to pink, near Red-Purple Group 57C, when the blossoms are fully mature. The petals have a small-sized yellow spot at the base that is Yellow Group 10A on both surfaces.

*Petal configuration.*—Possess some reflexing and undulation.

*Fragrance.*—Weak.

*Petal number.*—5.

*Filaments.*—Yellow in coloration.

*Pollen.*—Beige-yellow in coloration.

*Style.*—Short, and yellow-green in coloration with weak pubescence on the upper one half.

*Stigma.*—Commonly disposed below the anthers.

*Petal drop.*—Petals comonly detach cleanly and exhibit a good petal drop.

*Receptacle.*—Small and pear-shaped with prickles.

*Lasting quality.*—Approximately 5 to 7 days on the plant depending upon the environmental conditions.

*Duration.*—Blossoms commonly are formed beginning in mid-season (e.g., approximately June 24th) continuously over a period of 10 weeks or more when grown in the landscape.

*Hips.*—Round orange-red shiny hips commonly are formed on an abundant basis.

Development:

*Blossoming.*—Continuous.

*Hardiness.*—Has survived winter temperatures of −28° C. to −30° C.

*Resistance to diseases.*—Is resistant to powdery mildew [*Sphaerothea pannosa* (Wallr. ex Fr.) Lev.] and blackspot (*Diplocarpon rosae* Wolf.) during observations to date.

*Preferred mode of propagation.*—The use of softwood cuttings to produce self-rooted plants is recommended. For instance, softwood cuttings taken at the bud stage can be dipped in rooting powder (e.g., Stimroot No. 2, 0.4 percent indolebutyric acid of Plant Products, Bramalea, Ontario, Canada) and placed under mist for 3 to 4 weeks at 20 to 25° C. ambient temperature.

I claim:

1. A new and distinct variety of shrub rose plant characterized by the following combination of characteristics:

(a) exhibits an arching growth habit with attractive dark green foliage that bears glossiness on the upper surface, (b) forms attractive dark red single blossoms that tend to fade to pink when fully mature, (c) propagates well by the use of softwood cuttings, (d) exhibits good winter hardiness, (e) exhibits good resistance to powdery mildew and blackspot, and (f) is particularly well suited for growing as ornamentation in the landscape;

substantially as herein shown and described.

* * * * *